United States Patent
Ambrosen et al.

(10) Patent No.: US 6,558,681 B1
(45) Date of Patent: May 6, 2003

(54) COSMETIC PRODUCTS COMPRISING CREAM OF TARTER AND SODIUM BICARBONATE

(75) Inventors: Helen Ambrosen, Dorset (GB); Mark Constantine, Dorset (GB); Margaret Constantine, Dorset (GB)

(73) Assignee: Lush Limited, Dorset (GB)

( * ) Notice: Subject to any disclaimer, the term of this patent is extended or adjusted under 35 U.S.C. 154(b) by 0 days.

(21) Appl. No.: 09/913,624

(22) PCT Filed: Feb. 15, 2000

(86) PCT No.: PCT/GB00/00514

§ 371 (c)(1),
(2), (4) Date: Dec. 7, 2001

(87) PCT Pub. No.: WO00/47180

PCT Pub. Date: Aug. 17, 2000

(30) Foreign Application Priority Data

Feb. 15, 1999 (GB) .............................. 9903422

(51) Int. Cl.⁷ .............................. A61K 7/00; A61L 9/01
(52) U.S. Cl. ....................... 424/401; 424/76.1
(58) Field of Search .................... 424/401, 65, 76.1

(56) References Cited

U.S. PATENT DOCUMENTS 3,629,468 A    12/1971  Anderson .................... 424/44
4,127,645 A  * 11/1978  Witzel et al. ................. 424/44

FOREIGN PATENT DOCUMENTS

| FR | 1 540 469 |   | 9/1968 |
| FR | 2 549 723 |   | 2/1985 |
| GB | 1 492 660 | * | 11/1977 |
| GB | 1 507 356 |   | 4/1978 |
| GB | 1 492 660 |   | 11/1997 |
| JP | 4941548 |   | 4/1974 |
| JP | 61 225 117 | * | 6/1986 |
| JP | 61225117 A |   | 10/1986 |

* cited by examiner

Primary Examiner—Jose' G. Dees
Assistant Examiner—Konata M. George
(74) Attorney, Agent, or Firm—Westman, Champlin, & Kelly, P.A.

(57) ABSTRACT

A cosmetic product and the like, including a deodorant, comprising a dicarboxylic acid and sodium bicarbonate preferably dihydroxybutanedioic acid and sodium bicarbonate and most preferably comprising cream of tarter and sodium bicarbonate. A mixture of sodium bicarbonate, cream of tarter and water forms a paste which hardens into a solid over a period of a few hours. The mixture provides a solid material which is highly stable. It does not dissolve quickly and does not effervesce, but instead remains essentially stable and retains it's solid form.

37 Claims, No Drawings

COSMETIC PRODUCTS COMPRISING CREAM OF TARTER AND SODIUM BICARBONATE

The present application claims priority of International patent Application No. PCT/GB00/00514, filed Feb. 15, 2000, and published in English, which claims priority to Great Britain patent Application No. 9903422.5, filed Feb. 15, 1999, the contents of which are hereby incorporated by reference in their entirety.

The present invention relates to cosmetic products and the like, including deodorants.

There is a continuing interest in so-called natural products which do not use synthetic chemical preparations and, generally, an increased awareness of environmental issues. The present invention has been made against this background.

According to one aspect of the present invention there is provided a cosmetic product having the form of a solid and comprising cream of tarter and sodium bicarbonate.

According to another aspect of the present invention time is provided a cosmetic product having the form of a solid and comprising dihydroxybutanedioic acid and sodium bicarbonate.

According to another aspect of the present invention there is provided a cosmetic product having the form of a solid and comprising a dicarboxylic acid and sodium bicarbonate.

According to another aspect of the present invention there is provided a deodorant having the form of a solid and comprising cream of tarter and sodium bicarbonate.

According to another aspect of tie present invention there is provided a cosmetic product deodorant having the form of a solid and comprising dihydroxybutanedioic acid and sodium bicarbonate.

According to another aspect of the present invention there is provided a cosmetic product deodorant having the form of a solid and comprising a dicarboxylic acid and sodium bicarbonate.

Embodiments of the present invention will now be described in more detail and by way of further example only.

Although the invention relates to cosmetic products generally, a description will be given in relation to a deodorant product.

One form of conventional deodorant for personal hygiene is that often referred to as a deodorant stick. Such products usually consist of a viscous gel or semi-solid deodorant material which is housed in rigid plastics container with a mechanism for incrementally propelling the deodorant material from the container as the material is used. The deodorant material is not sufficiently solid to be self supporting and the rigid container not only provides containment but also functions to control the quantity of deodorant which is applied to the users body, by control of the amount of deodorant material presented beyond the end of the container by the propelling mechanism.

A mixture containing sodium bicarbonate as the main component has been used in bath products. Such products effervesce strongly when immersed in water and dissolve quickly. That is, they are highly unstable in the presence of water, as is required by their intended use. It is therefor highly surprising that a mixture consisting of sodium bicarbonate as the main component, cream of tarter and water should provide a solid material which is highly stable. A mixture of 60% sodium bicarbonate, 30% cream of tarter and 10% water forms a paste which hardens into a solid over a period of a few hours. The resultant solid material can be dipped in water and patted on to the skin. A small amount of sodium bicarbonate is thus deposited on the skin and absorbs odours thereon. Although dipped in to water during this process, the solid material does not dissolve quickly and does not effervesce, but instead remains essentially stable and retains it's solid form. The material is thus suitable for repeated use, in stark contrast to the known bath products.

As mentioned above, in preparation the product is in the form of a paste which subsequently hardens in to a stable solid. The final product can thus very easily be formed in many useful and/or novelty shapes. Moreover, there is no requirement for a rigid plastics container; which reduces costs and avoids environmental pollution caused by the disposal of empty containers.

One example of the relative ratios of the components is given above. These can of course be varied, the requirement being only that a useable solid form product results. It appears most preferable for the sodium bicarbonate to constitute 50% to 60% of the initial mixture, cream of tarter 30% to 35% and water 10% to 15%. Small amounts of additives may be included, such as a fragrance and/or colourant. Stated generally, a broad range would be for the sodium bicarbonate to constitute 50% to 70% of the initial mixing cream of tarter 25% to 35% and water 0.1% to 20%. Slightly more preferable is for the sodium bicarbonate to constitute 50% to 67% of the initial mixture, cream of tarter 25% to 35% and water 0.2% to 10%.

Although the above description has been of a deodorant for personal hygiene, as an example of a personal cosmetic product, it will be appreciated that the deodorant is equally well suited to other uses, for example as a fridge odour eater. Equally, although described above as a personal deodorant, the use of additives as mentioned can result in the product being considered as providing a different function. Clearly a relevant example is the provision of a solid fragrance/perfume, which can be applied in exactly the same manner as described above with respect to the solid deodorant, a further example is the use of rouge as an additive and the cosmetic product resulting therefrom.

Cream of tartar is readily available and has be used in the above examples for ease of reference. Cream of tartar is of course a form of tartaric acid, itself also known as dihydroxybutanedioic acid, a dicarboxylic acid and one of the most widely distributed of plant acids. Cream of tartar is a common name for potassium hydrogen tartar. Other common names include Crystals of Argolis. The substance is usually obtained from by-products of wine fermentation. In partially purified form, tartar was known to the ancient Greeks and Romans and the free acid was first isolated in 1769. It's use in a cosmetic product is, however, not known to have been previously proposed. The present invention is not limited to the use of cream of tartar, other forms of organic acid being considered equally applicable.

The invention includes products in which part of the sodium bicarbonate is replaced by one or more clays, such as Kaolin or Calamine. The water content can be replaced, wholly or partially, by humectants to provide a moisturizing effect, or fruit juices and/or solid fruit to carry these on to the skin.

Beneficial additives can include one or more essential oils and even fatty materials such as Cocoa Butter or Shea Butter. For example, a deodorant as described but including Cocoa Butter as an additive enhances the suitability of the product for application to drier skins.

Colouring additives can also be used to provide not only a general aesthetic appeal but also marketing possibilities by incorporating a brand name or the like with an effect similar to the lettering in edible rock or candy. This can be achieved by moulding the letters from a paste incorporating a colouring additive and then moulding the paste of the main body around the individual letters.

What is claimed is:

1. A cosmetic product having the form of a solid and comprising cream of tartar and sodium bicarbonate, and prepared from a mixture including 0.1% to 20% by weight of water.

2. A cosmetic product as claimed in claim 1 and prepared from a mixture including 50% to 60% by weight of sodium bicarbonate.

3. A cosmetic product as claimed in claim 1 and prepared from a mixture including 10% to 15% by weight of water.

4. A cosmetic product as claimed in claim 1 and prepared from a mixture including 30% to 35% by weight cream of tartar.

5. A cosmetic product as claimed in claim 1 and further including one or more additives.

6. A cosmetic product as claimed in claim 5 including a fragrance as an additive.

7. A cosmetic product as claimed in claim 5 including a fatty material as an additive.

8. A cosmetic product as claimed in claim 1 further including a fruit juice.

9. A cosmetic product as claimed in claim 1 further including part of a fruit.

10. A cosmetic product as claimed in claim 1 further including Kaolin.

11. A cosmetic product as claimed in claim 1 further including Calamine.

12. A cosmetic product as claimed in claim 1 further including a humectant.

13. A cosmetic product as claimed in claim 1 further including a coloring additive providing lettering in the product.

14. A deodorant having the form of a solid and comprising cream of tarter and sodium bicarbonate, and prepared from a mixture including 0.1% to 20% by weight of water.

15. A deodorant having the form of a solid and comprising dihydroxybutanedioic acid and sodium bicarbonate.

16. A deodorant having the form of a solid and comprising a dicarboxylic acid and sodium bicarbonate.

17. A deodorant as claimed in claim 14 and prepared from a mixture including 50% to 60% by weight of sodium bicarbonate.

18. A deodorant as claimed in claim 14 and prepared from a mixture including 10% to 15% by weight of water.

19. A deodorant as claimed in claim 14 and prepared from a mixture including 30% to 35% by weight cream of tartar.

20. A deodorant as claimed in claim 14 and further including one or more additives.

21. A deodorant as claimed in claim 20 including a fragrance as an additive.

22. A deodorant as claimed in claim 20 including a fatty material as an additive.

23. A deodorant as claimed in claim 14 further including a fruit juice.

24. A deodorant as claimed in claim 14 further including part of a fruit.

25. A deodorant as claimed in claim 14 further including Kaolin.

26. A deodorant as claimed in claim 14 further including Calamine.

27. A deodorant as claimed in claim 14 further including a humectant.

28. A deodorant as claimed in claim 14 further including a coloring additive providing lettering in the product.

29. A method of manufacturing a cosmetic product comprising preparing a mixture of cream of tartar, sodium bicarbonate and water, and allowing the mixture to harden to provide the cosmetic product in the form of a solid.

30. A method as claimed in claim 29, wherein the mixture includes 0.1% to 20% by weight of water.

31. A method as claimed in claim 29, wherein the mixture including 50% to 60% by weight of sodium carbonate.

32. A method as claimed in claim 30, wherein the mixture includes 50% to 60% by weight of sodium carbonate.

33. A method as claimed in claim 29, wherein the mixture includes 30% to 35% by weight of cream of tartar.

34. A method as claimed in claim 30, wherein the mixture includes 30% to 35% by weight of cream of tartar.

35. A method as claimed in claim 29, wherein the mixture further includes one or more additives.

36. A cosmetic product having the form of a solid and comprising dihydroxybutanedioic acid and sodium bicarbonate.

37. A cosmetic product having the form of a solid and comprising a dicarboxylic acid and sodium bicarbonate.

* * * * *